United States Patent [19]

Augros

[11] Patent Number: 5,439,685
[45] Date of Patent: Aug. 8, 1995

[54] PHARMACEUTICAL COMPOSITION FOR THE PREVENTION OF SEXUALLY TRANSMITTED DISEASES

[75] Inventor: Jacques J. Augros, Villiers Le Bel, France

[73] Assignee: S S P L Safe Sex Products Licensing Societe Anonyme, Paris, France

[21] Appl. No.: 995,522

[22] Filed: Dec. 22, 1992

Related U.S. Application Data

[63] Continuation of Ser. No. 377,938, Jul. 11, 1989, abandoned.

[30] Foreign Application Priority Data

Jul. 11, 1988 [FR] France ................... 88 09418

[51] Int. Cl.$^6$ .................. A61K 9/107; A61L 15/44
[52] U.S. Cl. .................... 424/430; 424/431; 514/169; 514/841; 514/843; 514/931; 514/934; 514/937
[58] Field of Search ............... 424/430, 431; 514/931, 514/841, 934, 843, 169, 937

[56] References Cited

U.S. PATENT DOCUMENTS

| | | | |
|---|---|---|---|
| 4,230,686 | 10/1980 | Schopflin et al. | 424/22 |
| 4,582,717 | 4/1986 | von Bittera et al. | 424/431 |
| 4,795,425 | 1/1989 | Pugh | 604/349 |
| 4,922,928 | 5/1990 | Burnhill | 604/369 |
| 4,952,411 | 8/1990 | Fox, Jr. et al. | 514/169 |

FOREIGN PATENT DOCUMENTS

| | | |
|---|---|---|
| 81370 | 6/1983 | European Pat. Off. . |
| 0113998 | 7/1984 | European Pat. Off. . |
| 255902 | 2/1988 | European Pat. Off. . |
| 0285285 | 10/1988 | European Pat. Off. . |
| 0290307 | 11/1988 | European Pat. Off. . |
| 1161484 | 8/1969 | United Kingdom . |
| 1185943 | 3/1970 | United Kingdom . |
| 2153686 | 8/1985 | United Kingdom . |

*Primary Examiner*—Thurman K. Page
*Assistant Examiner*—Amy Hulina
*Attorney, Agent, or Firm*—Jacobson, Price, Holman & Stern

[57] ABSTRACT

A pharmaceutical composition for the prevention of sexually transmitted diseases, intended to be contacted with a mucosa. The composition contains, on the one hand, at least one constituent active against the viruses and bacteria responsible for the said sexually transmitted diseases and, on the other hand, a product inhibiting the penetration of the active constituent across a mucosa, in combination with a pharmaceutically acceptable vehicle adapted to the topical administration of this composition. Advantageously, the product inhibiting penetration is a film-former capable of forming a film with which the active constituent or constituents are associated.

11 Claims, No Drawings

PHARMACEUTICAL COMPOSITION FOR THE PREVENTION OF SEXUALLY TRANSMITTED DISEASES

This is a continuation of application Ser. No. 07/377,938, filed Jul. 11, 1989 which was abandoned.

BACKGROUND OF THE INVENTION

The present invention relates to the prevention of sexually transmitted diseases, referred to below by the abbreviation "STD's", such as AIDS in particular.

The most common STD's are due in particular to viruses, bacteria, parasitic organisms and fungi. In the face of the development of these diseases, there exists today no means of prevention of sufficient effectiveness and able to offer an alternative to the use of condoms, whose imperfections and inconveniences are nevertheless known.

DESCRIPTION OF THE PRIOR ART

Now it is known that various chemical agents possess a certain effectiveness against the microorganisms responsible for the STD's. Among the agents most commonly used can be cited dimethylalkylbenzalkonium chloride or benzalkonium chloride and nonylphenololyoxyethylene or nonoxynol 9.

However, these products are only relatively effective in the sense that, on the one hand their spectrum of action is narrow since they cover only some of the microorganisms responsible for the STD's, and on the other hand the time required for their action is long and therefore unacceptable when it is a question of preventing the STD's.

It is known for example that infection by the AIDS virus can occur from the very first minutes of its contact with healthy mucosae. On the other hand, the inactivation of this virus by benzalkonium chloride at a concentration of 1% only occurs after a contact time of at least ten minutes, which leaves a possibility of infection which is extremely large and therefore unacceptable in practice.

As a result, the use of known products does now allow effective prevention of the STD's, even when they have virusidal properties.

In another connection it is known from the document EP-A-O 113 998 that derivatives of cholic acid—principally deoxycholic and dehydrocholic acids—can be used in the treatment of the viral infections caused by the herpes virus simplex I or II.

However, it is there a question of a therapeutic action and not a preventive one, whereas the proposal of the present invention is precisely to provide a means of prevention. The boundary between therapy and prevention is not always very clear-cut, but the understanding of the difference between these two modes of action is essential here, since it is the choice of the one or the other which conditions the determination of the pharmaceutical composition used, the use of the treatment, its form and its method of administration as well as the scope of its use. Unlike preventive action, which concerns healthy subjects, therapeutic action, such as that envisaged in the patent EP-A-O 113 998, produces its effects in a subject already affected. In this case, it is when the infection is visible or at least detectable, and consequently well established, that the illness can have recourse to a remedy. So it is possible to determine very precisely the places infected by the herpes virus simplex I or II, where the treatment must be applied, if one uses the topical method.

Now two modes of administration can be envisaged: parenteral or topical in the sense of a very localized application on the precise spot where the infection is situated.

In the present invention, topical administration means the application of a pharmaceutical composition not on a zone strictly delimited by a symptomatic infection but on the contrary over a wide zone, often complex and always imprecise since the infection which one wishes to prevent is therefore non-localized. Thus the expression "topically" used in the case of therapy and therefore in the patent EP-A-O 113 998 (treatment of a precise point already affected) must not be confused with the same expression used here in the case of prevention, whose significance, indicated above, is altogether different.

Moreover, when the objective is the prevention of the STD's, topical administration is preferred to parenteral administration because of the presence of certain compounds which are necessary for real effectiveness but must not be introduced into the organism. They can actually become toxic when they are absorbed at large doses and then metabolized by the organism.

It is finally necessary to note that in the patent EP-A-O 113 998, only the action on the herpes virus simplex I and II has been described, whereas the present invention relates to prevention against a broad spectrum of viruses responsible for STD's, of which the principal strains are for example:

the genital herpes I and II viruses
the AIDS HIV I and HIV II viruses
the hepatitis B virus
the papilloma virus, To this end the present invention implies the protection of wide complex zones.

Now the teaching of the patent EP-A-O 113 998 does not encourage the person skilled in the art to use one of the derivatives of cholic acid:

on the one hand, for effective preventive action during several hours which necessitates the application of a pharmaceutical composition, in a uniform and sufficient manner, on a poorly delimited zone, either healthy but liable to be infected or affected and therefore liable to infect a partner, on the other hand for a broad spectrum of viruses which correspond to manifestations different from those of herpes simplex and so of much more general effect.

The vagina is a mucosa which by its nature facilitates the transfer of substances just as well by emission to its own exterior as by absorption into the interior of the organism.

Now for an effective prevention of the STD's, the active constituent or constituents must not be absorbed by the organism, in particular by a vaginal mucosa.

In fact, up to the present it has not been possible to use certain substances for such prevention, although they are effective, because these substances diffuse rapidly into the organism.

SUMMARY OF THE INVENTION

It is accordingly an object of the present invention to provide a pharmaceutical composition containing one or more active constituents, effective for the prevention of the STD's.

It is a further object of the invention to provide a pharmaceutical composition permitting the topical protection of zones of high risk, such as the woman's vagina.

These objects in accordance with the present invention by providing a pharmaceutical composition for the prevention of the sexually transmitted diseases, intended to be contacted with a mucosa which comprises on the one hand at least one active constituent against the viruses or bacteria responsible for the said sexually transmitted diseases and on the other hand a product inhibiting penetration of the said active constituent across the mucosa, in combination with a pharmaceutically acceptable vehicle adapted to topical administration of this composition.

DETAILED DESCRIPTION OF THE PREFERRED EMBODIMENTS

The invention will be better understood by the following detailed description given by way of an indicative but non-limiting example.

The penetration inhibitor is preferably an inert and non-toxic agent capable of forming an insulating and protective film on the mocosae or on the skin.

Moreover, to be sufficient, the protection must be effective from the vaginal orifice onwards and cover the whole of the mucosa, which is very difficult to achieve because of the extremely numerous folds of the letter.

The pharmaceutical composition in accordance with the invention preferably contains an inert and nontoxic agent dispersing the active constituent or constituents in order to obtain a uniform and sufficient spreading-out of the composition.

Preferably, the penetration inhibiting agent and the dispersant agent contained in the composition in accordance with the invention comprise one and the same compound, especially from the silicones family.

The pharmaceutical composition of the present invention contains for example a salt of cholic acid as active constituent.

It is known that cholic acid is a natural constituent of the bile and is currently used, as well as its pharmaceutically acceptable salts, in therapy as choleretic agent.

The use is known, in accordance with the patent application EP-A-O 285 285, of a dispersant presented in this document as being "any agent able to reduce the interfacial tension in aqueous medium", in combination with a derivative of cholic acid for the treatment of viral infections. Knowing that the virus uses the proteins of the cell in which it lives as a parasite to form a shell round its chain of nucleic acid (DNA or RNA), the anti-viral action of the dispersant, postulated in the patent application EP-A-O 285 285, resides in the rupture of the shell of the virus which, being no longer able to invade other cells, is thus destroyed.

It is important to make clear here that the dispersant, whose action is indicated above, enters into a pharmaceutical composition administered parenterally. The pharmaceutical composition containing the said dispersant is injected directly into the bloodstream.

The action of the dispersing agent in combination with one or several active constituents in the pharmaceutical composition in accordance with the present invention is completely different.

Here, in fact, this agent does not act directly on the virus, contrary to what is described in the above patent application.

The composition in accordance with the invention is intended for topical administration, contrary to the methods of administration (parenteral and oral) described in the patent application EP-A-O 285 285.

The principal property of the film-forming agent contained in the composition in accordance with the invention is to form on the whole surface of the zone which one wishes to protect a uniform and insulating film which plays the role of a barrier:

it inhibits the penetration of the active constituent into the organism, preventing it from being metabolized; after spreading out, it leaves the active constituent the time to act;

it prevents the diffusion of the viruses responsible for the STD's across the mucosa. The undesirable viruses are thus maintained in contact with the active constituent which can destroy them;

its insulating and protective role is a double one in this sense, that on the one hand it protects a healthy woman against a possible infection by an affected partner and that on the other hand, in the case where the woman is affected, it protects the partner by the same insulating effect.

The combination of the film-forming effect and the dispersant effect permits a spreading out over the whole surface of the folds constituting a vaginal mucosa.

The salt of cholic acid used in the pharmaceutical composition in accordance with the invention is preferably sodium cholate.

Sodium cholate is a powerful virucide and bactericide. This compound is a biological substance without toxicity and active even at low concentrations. The quantity of sodium cholate to use in the pharmaceutical composition in accordance with the invention is advantageously between 0.2 and 1.5%, and preferably between 0.25 and 1% by weight relative to the total weight of the composition.

The film-forming and dispersing agent preferred for the purposes of the invention is dimethylpolysiloxane, which also possesses an anti-adhesive effect reinforcing the insulating effect of the film.

The quantity of dimethylpolysiloxane contained in the pharmaceutical composition which is the object of the present invention is of the order of 3.5% by weight relative to the total weight of the composition.

It is notable that, in accordance with the invention, the quantity of the film-forming agent is very large by comparison with the amounts of the active constituent.

This is due to the fact that one has sought the formation of a film not only over the whole extent of the surface to be protected (which is large in the case of the vaginal mucosa) but also with sufficient compactness to obtain the effect of an insulating barrier which is as effective as possible, and that for two purposes:

to reduce, (but, it is hoped, to avoid altogether) the risks of transfer of pathogenic agents as much from as in the direction of the mucosa, to prevent the absorption by the mucosa of the active constituents associated with the film and thus to keep in place the said active constituents where their topical action is necessary.

This quantity can for preference be increased rather than diminished by the fact that the film-forming effect has a tendency to increase with the concentration.

The pharmaceutically acceptable vehicle which is suitable for the purposes of the invention is a conventional vehicle adapted to administration by the topical method. In the case of protection of the vaginal mucosae, the vehicle must be suitable for internal and prolonged use.

The person skilled in the art will for preference choose an aqueous vehicle which will allow adhesion and dilusion with the natural fluids present.

For advantageous application, the composition in accordance with the invention can contain in addition a buffering agent such as hydrochloric acid in order to be able to adjust the pH to about 4.7. This value enables one to have regard to the vaginal flora and the Doederlein bacillus. The non-destruction of the Doederlein bacillus is very important since it possesses essential defensive properties against the genital infections. It is therefore necessary to preserve it.

The pharmaceutical composition in accordance with the invention can be presented in the form of solutions (vaginal douches), creams or gels.

The person skilled in the art will choose a pharmaceutically acceptable vehicle adapted to the presentation employed.

The form in which the composition in conformity with the invention is presented is linked to its method of use. This composition must possess, in addition, a certain viscosity adapted to the manner in which it will be used.

To this end, the pharmaceutical composition in accordance with the invention contains, in addition, a thickening agent enabling a suitable rheological behaviour to be obtained.

Among the conventional thickening agents, the compound preferred for the purposes of the invention is hydroxypropylmethylcellulose, sold under the trade name "Métholose 60 SH 4000" by the SEPPIC company, 70 Avenue des Champs-Elysées, 75008 Paris (France).

This thickening enables the viscosity to be adjusted to the degree best adapted to the form of the composition (solution, cream, gel etc.). The viscosity thus obtained is not notably modified when the pH of the composition varies in the course of its production.

The importance of this agent will be better understood with the aid of the application presented below.

Thus, the concentrations most frequently used for a pharmaceutical composition in accordance with the invention are summarized in Table I:

Table I 0.25 to 1% by weight of sodium cholate
3.5% by weight of dimethylpolysiloxane
4% by weight of hydroxypropylmethylcellulose
hydrochloric acid: amount necessary for pH=4.7
water: amount required for 100%.

In accordance with a more developed way of carrying out the invention, several active constituents are combined, notably for reinforcing the action of sodium cholate, in particular on certain bacteria.

Consequently the composition in accordance with the invention can contain one or more virucidal and bactericidal agents, also having spermicidal properties, in combination with sodium cholate and the film-forming dispersing agent. Among these virucidal, bactericidal and spermicidal agents, benzalkonium chloride and/or nonoxynol 9 are chosen for preference.

It is to be noted here that the possibility of using nonoxynol 9 illustrates the advantages obtained by the invention. Nonoxynol 9 can in fact develop a certain toxicity when it penetrates into the organism in large amounts because of its accumulation, especially in the kidneys. Moreover its capacity to transfer across a vaginal mucosa amounts to about 80%. But the use of nonoxynol 9 in a composition in accordance with the invention is entirely possible and without risk, thanks to the presence in this composition of the insulating film formed by the film-former, which is an inhibitor, combating thus the penetration of this active constituent into the organism.

The quantities used are preferably between 0.5 and 1% and 0.25 and 1% by weight relative to the total weight of the composition for benzalkonium chloride and nonoxynol 9 respectively.

Thus, a pharmaceutical composition which is especially suitable for the purposes of the invention preferably contains the amounts indicated in Table II below:

Table II 0.25 to 1% by weight of sodium cholate
0.50 to 1% by weight of benzalkonium chloride
0.25 to 1% by weight of nonoxynol 9
3.5% by weight of dimethylpolysiloxane
4% by weight of hydroxypropylmethylcellulose
hydrochloric acid: amount necessary for pH=4.7
water: amount required for 100%.

The pharmaceutical composition prepared in accordance with the proportions of Table II above is especially suitable for the prevention of the STD's because of its specificity, and enables a very effective protection to be obtained.

Its action is in fact simultaneously virucidal, spermicidal and bactericidal.

It thus permits effective inactivation of the viruses responsible for the STD's but also the bacteria and fungi responsible for the STD's, among which can be quoted Staphylococcus aureus,
Candida albicans,
Streptococcus agalactiae,
Neisseria gonorrhoeae,
Garnella vaginalis,
Trichomonas vaginalis, The three active agents combined in the composition of Table II act in a complementary way and therefore possess a very wide spectrum of action.

One can quote as example the effective action of nonoxcynol 9 on Chlamidia trachomatis which nevertheless causes a very large increase of infections due to Candida albicans. Now benzalkonium chloride, also present in the composition, has for its part a very marked action on Candida albicans.

For the prevention of the STD's, the pharmaceutical composition in accordance with the invention can advantageously be used in combination with a vaginal tampon such as that described by the inventor in the patent FR-A-2 614 525, the disclosure of which is hereby incorporated by reference. This tampon removes the disadvantages inherent in the conventional tampons used in contraception: difficulty of extraction, irritation and lack of unobtrusiveness. This results from the presence on its body of at least one recess, which serves as a device for catching on to and extraction.

For an advantageous application of the pharmaceutical composition in accordance with the present invention, the tampon must also possess characteristics relating to its composition and its mode of preparation.

Thus, a tampon used as support for the pharmaceutical composition according to the invention, for the prevention of the STD's, consists of a foam of the open-cell type, such as for example an ether polyurethane foam.

The ether polyurethane foam making up a tampon used for the purposes of the invention has a density of preferably between 15 and 28.

On the other hand, the ether polyurethane foam shows a rupture strength of preferably between 70 and 150 kiloPascal (KPa).

Finally, the mean dimension of the cells in the ether polyurethane foam is preferably between 0.67 and 0.53 millimeters (mm).

For an advantageous application of the invention, the tampon is prepared in such a way that it does not include a "skin", that is to say an external surface more or less continuous and practically without open cells.

To do this, the tampon is cut from a slab of convenient thickness, itself cut from a block previously freed from its external "skin" by a sawing operation.

It is for the person skilled in the art to choose, having regard to the criteria explained previously, the shape and dimensions of the tampon adapted to the anatomy of the female user.

The pharmaceutical composition in accordance with the invention preferably takes the form of an aqueous gel; aqueous because of the part of the body where the tampon is used. For it is a matter of internal use in a very sensitive zone: the vaginal mucosa, which must not be damaged or irritated. On the other hand, this gel form is perfectly adapted to retention within the tampon. For the composition must not, for example, leave the tampon too copiously when the user exerts pressure on it to introduce it into the vagina. Since the tampon must moreover be preserved and above all remain effective for quite a long time, for at least several hours, the form of the pharmaceutical composition which impregnates the tampon must be such that it is not excreted excessively during the first minutes of its application. The use of a gel is important because it removes this drawback which would impair efficiency. This gel form also permits, because of its particular viscosity, good contact with the mucosae as well as uniform and sufficient spreading out on them.

The preceding underlines also the importance of the role of the thickener as regards the necessary viscosity which the gel used to impregnate the tampon must have.

The quantity of aqueous gel in accordance with the invention necessary for impregnating a tampon depends on the dimensions and the composition of the latter. However, experience shows that it is preferable that the tampon is not completely impregnated, because on the one hand there would be an excretion of a large quantity of gel when the user compresses the tampon in order to introduce it to the vagina, and on the other hand it is necessary to allow the natural fluids the possibility of being absorbed (by substitution) and of being neutralized. The quantity of gel necessary to impregnate the tampon proves to meet the above conditions when it is of the order of 25% of the total absorption volume of the tampon.

Each tampon is packaged individually in a waterproof capsule.

For a tampon of 45 mm diameter and 20 mm thickness, a capsule is chosen having an internal diameter of 46 mm and a height of 24 mm. The clearance thus available is suitable for the mode of impregnation according to the invention.

The capsule has a peripheral rim 5 mm wide in order to allow the capsule to be provided with a protective cover by welding a lid to the rim.

The fitting of the cover is facilitated by the presence of the small free space existing above the tampon as a result of the difference in dimensions of the capsule (24 mm) and the tampon (20 mm).

The capsule can be made of a material of the polyvinyl type. As for the protective cover, it consists of an aluminum composite conventionally used for providing protective covers for plastic containers.

In accordance with the invention, the impregnation is carried out in the following way:

The required quantity of gel is placed in the bottom of the capsule. For a tampon of 45×20 mm, about 5 grams of gel is necessary. The latter then spreads as a thin layer over the whole surface of the capsule.

The tampon is then placed on this gel and the capsule is then fitted with its protective cover.

The gel penetrates into the tampon by capillarity.

The impregnation time is of the order of thirty seconds whereas the protective cover is fitted advantageously in a few seconds, immediately after the tampon is put down, that is to say before the impregnation proper is finished.

As a result, impregnation occurs during the subsequent conditioning operations. In other words, the impregnation is obtained "in hidden time".

The reverse step which would consist of depositing the gel on the tampon and not in the bottom of the capsule is not recommended if, as is logical, the internal volume of the capsule is close to the external volume of the tampon. In this case there is a strong probability of the gel being accidentally transferred onto the rim of the capsule when its protective cover is fitted. Since the protective cover must be fitted onto this rim, generally by welding, the interposition of the gel would constitute an obstacle to this welding, and all the more seriously since the gel contains a silicone. An insignificant quantity of silicone would be sufficient to cause an imperfect, that is to say non-watertight, fitting of the protective cover.

On another aspect, it is not essential to sterilize the tampon, because of its high content of virucidal and bactericidal agents.

Thus the use of a tampon impregnated with several active constituents combined presents, because of their complementary activities, advantages which are new and specifically adapted to prevention of the STD's.

Now the tampon, provided with open cells over the whole of its surface, allows the aqueous gel with which it is impregnated to be present and active from the time of application of the tampon with a view to introducing it to the vaginal orifice and to cover by degrees the whole of the vaginal mucosa as it advances, which are essential conditions for ensuring genuine and instantaneous protection.

The fraction of the aqueous gel extracted from the tampon during its advance is replaced at the periphery of the tampon by the gel initially contained in the cells of its central zone, thanks to the communications between the open cells. Moreover, because of this internal transfer, the quantity of gel leaving is greater during sexual intercourse, as a result of the movements which it implies, which is particularly favourable to the destruction of the germs contained in the vaginal medium as well as in the semen and the spermatazoa.

The physical spreading-out of the gel thus presents the advantage of being constant and regular, which it is not possible to achieve with an ordinary tampon. This comes to support the action of the dimethylpolysiloxane which permits, in parallel to its dispersant properties, the formation of a protective film on the mucosae and the skin. Associated with it is an insulating and hydrophobic effect as a result of the very nature of dimethylpolysiloxane, which belongs to the silicones family.

Given that the gel has a low concentration of active constituents and the film-forming agent has an inhibiting effect on the penetration of these constituents into the organism, the gel in accordance with the invention can be the object of repeated and prolonged use.

Thus, the user can renew the impregnated tampon as often as she wishes. One and the same tampon can be left in place for several hours without risk of producing irritation of the vaginal mucosae, even if forgotten.

Besides, it is recommended to retain it for at least six hours after the last sexual intercourse in order to ensure the best possible protection.

The presence of benzalkonium chloride in the formula in accordance with Table II comes to reinforce the existing action of the sodium cholate and avoids the risk of "toxic shock syndrome".

"Toxic shock syndrome" results from a rapid proliferation of Staphylococcus aureus when other pathogenic agents are destroyed. The gravity of this development results from the fact that Staphylococcus aureus produces violent toxine which very rapidly become fatal. Now benzalkonium chloride, like sodium cholate, has a marked effect on this very dangerous germ.

The impregnated tampon such as that described previously provides a double protection. For AIDS, for example, several cases can be imagined:

Sexual intercourse between a healthy woman and a partner with a symptomatic or seropositive disease: the female organism is insulated and protected by the film covering the vaginal mucosa. The active constituents destroy the infective agents contained in the semen or conveyed by the partner.

Sexual intercourse between a woman with a symptomatic or seropositive disease and a healthy partner: the covering of the vaginal cavity by the film of gel isolates the mucosa and the points of possible transfer of the viruses (erosions, intrusions). The virus cannot then leave the affected female organism. The gel ejected from the tampon settles also on the penis of the male partner; thus the film protects him by direct contact and by the effect of persistence of the skin.

Sexual intercourse between a woman and a partner, both with symptomatic or seropositive disease: the action of the gel avoids the serious reinfection of the seropositives by mutual insulation and destruction of the infective agents from the two sources.

This impregnated tampon is thus especially adapted to prevention against AIDS.

The impregnated tampon such as that described above can be employed for the prevention of the STD's, in addition to conventional means of contraception (contraceptive pills, coils etc.). It can act in particular without displacing the wires of certain coils.

It also presents the advantage of being unobtrusive. In fact, contrary to the condom, it is not noticed by the couple. In the case of the condom this factor is very limiting for the development of its use. As regards the present invention, this obstacle is removed.

Furthermore the impregnated tampon is available in a single-use tear-open package which enables it to be protected and preserved correctly, and thus confers great facility of use.

The application described above constitutes an especially preferred use of the pharmaceutical composition according to the invention, especially but not exclusively for combating the propagation of AIDS.

The invention will now be described in more detail with the aid of the following examples:

EXAMPLES

Products used

Sodium cholate sold by the Société CIPEC, 7 rue Lincoln, 75008 Paris (France).

Benzalkonium chloride sold under the trade name "REWOQUAT B 50" by the Société SCHERING, 5 rue Le Corbusier, 94150 Rungis (France).

Nonoxynol 9 sold under the trade name "SIMULSOL 930 NP" by the Société SEPPIC, 70 Avenue des Champs-Elysees, 75008 Paris (France).

Dimethylpolysiloxane sold under the trade name "A65 MEDICAL GRADE EMULSION" by the DOW CORNING CORPORATION, Midland, Mich. 48640 (United States of America).

Hydroxypropylmethylcellulose sold under the trade name "METHOLOSE 60 SH 4000" by the Sociéte SEPPIC, 70 Avenue des Champs-Elysées, 75008 Paris (France).

EXAMPLE I

Vaginal tampon impregnated with the aqueous gel in accordance with the formula of Table I

Tampon

This consists of an ether polyurethane foam, having the following characteristics:
density: about 22
rupture strength: about 130 KPa
mean dimension of the cells: 0.6 mm It measures 45 mm in diameter and 20 mm in thickness It has two recesses, as described in the patent FR-A-2 614 525.

Gel 5 grams of gel are necessary to impregnate a tampon having the above characteristics. (The total absorption volume of such a tampon is 20 grams).

The composition of the gel used is the following:

| | |
|---|---|
| sodium cholate | 0.025 g (0.5%) |
| dimethylpolysiloxane (35% solution) | 0.50 g (10%) |
| hydroxypropylmethylcellulose | 0.20 g (4%) |
| hydrochloric acid (1N) | amount giving pH = 4.7 |
| purified water | amount giving 5 g |

Preparation of the gel (This mode of operation can be used whatever the quantities used.)

In a stainless steel vessel (Vessel B), the sodium cholate is dissolved at ambient temperature in one half of the purified water. The dimethylpolysiloxane is then added. This solution is then mixed by agitation until a homogeneous solution is obtained. The products being surface-active, the mixture must be prepared at a low agitation speed.

In another stainless steel vessel with couble wall (Vessel A), half of the quantity of purified water is heated to 70° C. by circulating steam in the double wall. The hydroxypropylmethylcellulose is then introduced and dispersed with agitation until a homogeneous gel is obtained. This gel is then cooled to ambient temperature by circulation of cold water in the double wall of the vessel.

The solution obtained in vessel B is added progressively at ambient temperature to the gel prepared in the vessel A, with agitation, until a homogeneous gel is obtained.

The pH is adjusted by addition of a 1N solution of hydrochloric acid in sufficient amount to reach a pH of 4.7.

The total mass of gel is adjusted to 5 grams by addition of purified water in sufficient amount.

Impregnation of the tampon

The gel obtained above is placed at the bottom of a capsule having an internal diameter of 46 nm, a height of 24 mm and a peripheral rim 5 mm wide.

The tampon is placed on the gel and the latter penetrates into the tampon by capillarity.

The capsule is fitted with a protective cover by welding a lid to it, so as to make it watertight.

EXAMPLE II

Vaginal tampon impregnated with the aqueous gel according to the formula of Table II Tampon This has the same characteristics as that of Example I.

Gel 5 grams of gel are necessary to impregnate the tampon. The composition of the gel used is the following:

| | |
|---|---|
| sodium cholate | 0.025 g (0.5%) |
| benzalkonium chloride | 0.050 g (1%) |
| nonoxynol 9 | 0.025 g (0.5%) |
| dimethylpolysiloxane (35% solution) | 0.50 g (10%) |
| hydroxypropylmethylcellulose | 0.20 g (4%) |
| hydrochloric acid (1N) | amount giving pH = 4.7 |
| purified water | amount giving 5 g (4 to 4.2 g) |

Preparation of the gel

This is carried out in the same way as for Example 1. The benzalkonium chloride and nonoxynol 9 are added at the same time as the dimethylpolysiloxane.

Impregnation of the tampon

This is identical to that of Example I.

PHARMACOLOGICAL PROPERTINS

A -Virucidal properties

By determining the activity of reverse transcriptase in a solution infected with the AIDS HIV I virus, observations were made of the inhibition of the enzymatic agent of the virus, (a) by sodium cholate under the following conditions:

| Concentration of sodium cholate, % | Inhibition of reverse transcriptase, % | Treatment time, min. |
|---|---|---|
| 0.04 | 70 | 15 |
| 0.25 | 90 | 5 |

-continued

| Concentration of sodium cholate, % | Inhibition of reverse transcriptase, % | Treatment time, min. |
|---|---|---|
| 0.50 | 99 | 1 |

(b) by the gel whose composition corresponds to that of Example II:

| Concentration of gel (volume/volume) | Inhibition of reverse transcriptase, % | Treatment time, min. |
|---|---|---|
| $10^{-6}$ | 5 | |
| $10^{-5}$ | 7 | |
| $10^{-4}$ | 99 | |
| $10^{-3}$ | 100 | less than 2 |
| $10^{-2}$ | 100 | less than 2 |

B-Bactericidal properties

The gel whose composition corresponds to that of Example II shows at 32° C. the following bactericidal activity

| Strains | Antiseptic concentration (volume/volume) | Contact time necessary (minutes) |
|---|---|---|
| Staphylococcus aureus CIP 53127 | 0.5% | 5 |
| Candida albicans CIP 1180.79 | 5% | 5 |
| Streptococcus agalactiae CIP 55 118 | 0.5% | 5 |
| Neisseria gonorrhoeae CIP 79 18 | 0.1% | 5 |
| Garnella vaginalis CIP 7074 | 0.5% | 5 |

The bacterial strains quoted in the table represent species responsible for sexually transmitted vaginal infections.

The minimum antiseptic concentration according to the French Pharmacopoeia is 5% (gram/milliliter) in 15 minutes.

C-Antiparasitic properties

At a concentration of 0.5% (gram/milliliter) in water with a contact time of 5 minutes at 37° C., the gel (whose composition corresponds to that of Example II) has an immediate antiparasitic effect which causes the population of Trichonoma vaginalis to fall by a factor of at least 1000.

What is claimed is:

1. A pharmaceutical composition for preventing the transmission of sexually transmitted diseases, comprising in combination, a vaginal tampon containing an active agent being selected from the group consisting of cholic acid and salts of cholic acid; and dimethylpolysiloxane in the form of an emulsion and being present in an amount effective to form a substantially uniform film coating on the vaginal mucosa and to inhibit penetration of said active agent across the vaginal mucosa; wherein said vaginal tampon comprises an open cell foam.

2. A pharmaceutical composition for topical application to the vaginal mucosa for preventing the transmission of sexually transmitted diseases, said composition comprising, based on the total weight of the composition comprising:

a) 0.25 to 1% by weight of an agent active against microorganisms responsible for sexually transmitted diseases, said active agent being sodium cholate, b) 3.5% by weight dimethylpolysiloxane as a film forming agent and a dispersant, said dimethylpolysiloxane being in the form of an emulsion to form a substantially uniform film coating on the mucosa and to inhibit penetration of said active agent across the mucosa;

c) 0.5 to 1% by weight benzalkonium chloride and 0.25 to 1% by weight nonoxynol 9 acting as spermicidal agents; and d) 4% by weight hydroxymethylpropylcellulose acting as a thickening agent suitable for typical application; sufficient hydrochloric acid to adjust the pH of the composition to about 4.7; and balance water.

3. A pharmaceutical composition for preventing the transmission of sexually transmitted diseases, comprising in combination, a vaginal tampon containing an active agent being selected from the group consisting of cholic acid and salts of cholic acid; at least one spermicidal agent and dimethylpolysiloxane in the form of an emulsion and being present in an amount effective to form a substantially uniform film coating on the vaginal mucosa and to inhibit penetration of said active agent across the vaginal mucosa; wherein said vaginal tampon comprises an open cell foam.

4. A pharmaceutical composition comprising in combination a vaginal tampon as claimed in claim 1 wherein said vaginal tampon comprises a polyurethane ether foam having a density between 15 and 28, a rupture strength between 70 and 150 KPa and a cell dimension between 0.67 and 0.53 mm.

5. A pharmaceutical composition comprising in combination a vaginal tampon as claimed in claim 1 wherein said vaginal tampon is free of a surface skin so as to present open cells over the entire surface thereof.

6. A pharmaceutical composition comprising in combination a vaginal tampon as claimed in claim 1 further comprising a thickening agent; wherein said thickening agent is hydroxymethylpropylcellulose.

7. A pharmaceutical composition comprising in combination a vaginal tampon as claimed in claim 6, based on total weight of the composition comprises, 0.25 to 1.0% by weight of active agent, 3.5% by weight dimethylpolysiloxane in the form of an emulsion, 0.75 to 2.0% by weight spermicidal agent and 4% by weight thickening agent.

8. A pharmaceutical composition comprising in combination a vaginal tampon as claimed in claim 1, wherein the active agent is sodium cholate and the concentration of dimethylpolysiloxane is 3.5% by weight.

9. A pharmaceutical composition comprising in combination a vaginal tampon as claimed in claim 1, wherein said pharmaceutical composition comprises sodium cholate, dimethylpolysiloxane emulsion, hydroxymethylpropylcellulose, benzalkonium chloride, nonoxynol 9 and water.

10. A pharmaceutical composition comprising in combination a vaginal tampon as claimed in claim 9, based on total weight of the composition comprises, 0.25 to 1.0% by weight sodium cholate, 3.5% by weight dimethylpolysiloxane in the form of an emulsion, 0.5 to 1.0% by weight benzalkonium chloride; 0.25 to 1.0% by weight nonoxynol 9 and 4% by weight hydroxymethylpropylcellulose; sufficient hydrochloric acid to adjust the pH of the composition to about 4.7; and balance water.

11. A pharmaceutical composition comprising in combination a vaginal tampon as claimed in claim 1, wherein said vaginal tampon has at least one recess for use in inserting and extracting said vaginal tampon from the vagina.

* * * * *